(12) United States Patent
Cunningham

(10) Patent No.: US 7,179,277 B2
(45) Date of Patent: Feb. 20, 2007

(54) SURGICAL NEEDLE

(75) Inventor: Scott Cunningham, Cheshire, CT (US)

(73) Assignee: Tyco Healthcare Group LP, North Haven, CT (US)

(*) Notice: Subject to any disclaimer, the term of this patent is extended or adjusted under 35 U.S.C. 154(b) by 182 days.

(21) Appl. No.: 10/621,759

(22) Filed: Jul. 17, 2003

(65) Prior Publication Data

US 2004/0059380 A1 Mar. 25, 2004

Related U.S. Application Data

(60) Provisional application No. 60/396,941, filed on Jul. 17, 2002.

(51) Int. Cl.
*A61B 17/00* (2006.01)
*A61B 17/06* (2006.01)

(52) U.S. Cl. .......................... 606/223; 289/16

(58) Field of Classification Search ..... 112/80.03–222; 289/16; 606/222–227
See application file for complete search history.

(56) References Cited

U.S. PATENT DOCUMENTS

| | | |
|---|---|---|
| 20,409 A | 6/1858 | Jas |
| 461,602 A | 10/1891 | Boult |
| 1,599,059 A | 9/1926 | Morton |
| 3,038,475 A | 6/1962 | Orcutt |
| 3,238,942 A | 3/1966 | Lincoff |
| 4,513,747 A | 4/1985 | Smith |
| 4,524,771 A | 6/1985 | McGregor et al. |
| 4,660,559 A | 4/1987 | McGregor et al. |
| 4,799,484 A | 1/1989 | Smith et al. |
| 4,932,961 A | 6/1990 | Wong et al. |
| 5,002,565 A | 3/1991 | McGregor |
| 5,041,127 A | 8/1991 | Troutman |
| 5,100,432 A | 3/1992 | Matsutani |
| 5,330,441 A | 7/1994 | Prasad et al. |
| 5,342,397 A | 8/1994 | Guido |
| 5,403,344 A | 4/1995 | Allen |
| 5,415,707 A | 5/1995 | Bendel et al. |
| 5,464,422 A | 11/1995 | Silverman |
| 5,477,604 A | 12/1995 | Smith et al. |
| 5,539,973 A | 7/1996 | Smith et al. |
| 5,630,268 A | 5/1997 | Smith et al. |
| 5,644,834 A | 7/1997 | Smith et al. |
| 5,661,893 A | 9/1997 | Smith et al. |
| 5,683,416 A | 11/1997 | McGregor et al. |
| 5,693,072 A | 12/1997 | McIntosh |
| 5,701,656 A | 12/1997 | Smith et al. |
| 5,730,732 A | 3/1998 | Sardelis et al. |
| 5,776,268 A | 7/1998 | McJames et al. |
| 5,797,961 A | 8/1998 | Smith et al. |
| 5,913,875 A | 6/1999 | Smith et al. |
| 5,985,355 A | 11/1999 | Walther et al. |
| 6,018,860 A | 2/2000 | Smith et al. |
| 6,214,030 B1 | 4/2001 | Matsutani et al. |
| 6,252,195 B1 | 6/2001 | Mosavi et al. |
| 6,322,581 B1 | 11/2001 | Fukuda et al. |

*Primary Examiner*—Vy Bui

(57) ABSTRACT

A surgical needle having a base portion defining a root diameter and a tapered end portion extending from said base portion to a pointed end, the tapered end portion defining at least a first and second region, wherein the first region having an average taper ratio of approximately 2.76:1 and the second region having an average taper ratio of approximately 5.65:1.

8 Claims, 1 Drawing Sheet

SURGICAL NEEDLE

Figure 1:
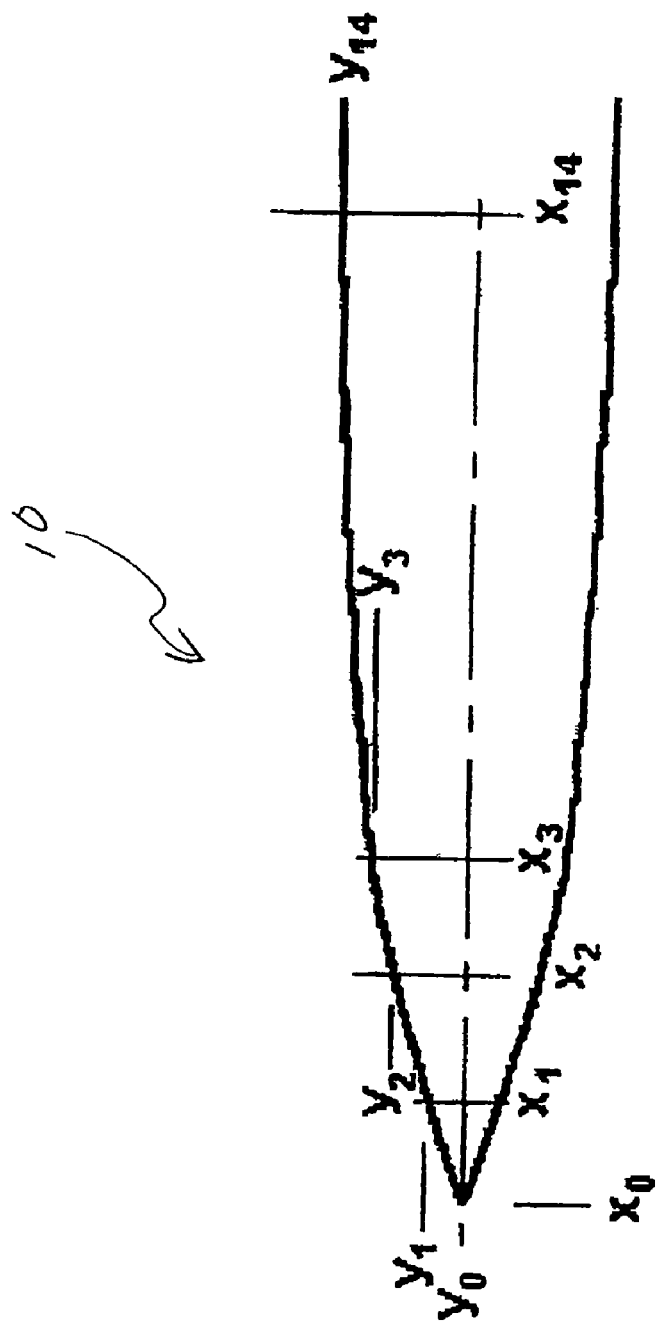

The present application claims priority to U.S. Provisional Application Ser. No. 60/396,941 entitled Surgical Needle which was filed on Jul. 17, 2002, the entire contents of which are hereby incorporated by reference.

BACKGROUND

1. Technical Field

The present invention relates to surgical needles.

2. Background of Related Art

Surgical suture needles are well known in the medical arts and include primarily two types of needles, taper point needles and cutting edge needles. A taper point type surgical needle includes a proximal end portion defining a suture-mounting portion having a hole or channel to which a suture is to be attached, an intermediate portion defining a main body portion having a generally uniform cross-sectional area throughout an entire length thereof, and a distal end portion defining a tapered portion whose cross-sectional area decreases progressively toward a pointed distal end of the suture needle. Cutting edge needles also taper to a piercing point, however, unlike taper point needles, these needles include one or more cutting edges with an otherwise smooth outer surface.

In the design of either taper point or cutting edge surgical needles it is generally desirable for the needles to exhibit favorable strength and ease of penetration characteristics. It is desirable for a surgical needle to be sufficiently strong in order to penetrate tissue which is being sutured without bending or breaking during a surgical procedure. It is also desirable for the surgical needle to easily penetrate and smoothly pass through the tissue being sutured. The amount of force required for the surgical needle to penetrate tissue includes the force required for the engagement of the tip of the needle and the force required for the widening of the hole. The force required for a taper point type surgical needle to widen the hole is greater than a cutting edge needle since the taper point type needle merely dilates the hole and does not cut the hole as would a cutting edge type needle.

Taper point surgical needles typically have a taper from a middle section of the needle body which ends in a distal piercing point. The taper is often expressed as a ratio of the length of the taper section to the diameter of the wire used to form the needle. It is known that the higher the taper ratio is, the more slender the taper, and thus the resistance to penetration and/or piercing through tissue will typically be lessened. However, the more slender the taper, the mechanical strength for needles manufactured from the same material will be lessened. The converse is also to be expected for needles having lower taper ratios.

In practice, the piercing resistance which the suture needle receives from the tissue of the living body is at a maximum level when the surgical needle is piercing the skin of the tissue. This is due to the fact that the skin of the tissue has a greater rupture strength than the other parts or layers of the tissue. The resistance of the suture needle as the needle pierces through the skin of the tissue greatly depends on the degree of sharpness of the pointed end of the suture needle. Once the suture needle pierces the skin of the tissue, the piercing resistance is abruptly reduced regardless of the value of the cross-sectional area increase rate of the tapered portion.

In view of the above, it is apparent that the design techniques generally employed to meet the above two design criteria of strength and ease of penetration are often in conflict. As stated above, one approach to improve the strength of a needle is to increase the diameter or thickness of the needle. However, by increasing the thickness of the needle, the force necessary to penetrate the tissue is also increased, and the opening left in the tissue after passage of the needle is also enlarged. Similarly, ease of penetration can be improved by making the needle thinner. However, a reduction in the thickness of the needle will result in a corresponding reduction in the needles strength. Thus the design of a needle which exhibits favorable strength and penetration characteristics requires that certain tradeoffs be made in the two criteria to arrive at a needle with optimal overall performance.

Accordingly, there is a continuing need for surgical tapered needles exhibiting improved penetrating characteristics (i.e., resistance to penetration through tissue) and improved mechanical characteristics such as bending strength.

SUMMARY

A surgical needle is provided having a base portion defining a root diameter and a tapered end portion extending from said base portion to a pointed end, the tapered end portion defining at least a first and second region, wherein the first region having an average taper ratio of approximately 2.76:1 and the second region having an average taper ratio of approximately 5.65:1.

BRIEF DESCRIPTION OF THE DRAWING FIGURES

FIG. 1 is a cross-section profile of a tapered end portion of one illustrative embodiment of a surgical needle constructed in accordance with the present disclosure.

DETAILED DESCRIPTION OF PREFERRED EMBODIMENTS

The present disclosure is directed to a surgical needle having a distal end tapered tip portion which is characterized by having an increased taper ratio to substantially minimize the potential for tip breakage while maintaining sufficient penetration capability to achieve efficacious results. The surgical needle is intended for use in suturing delicate tissue in conjunction with, for example, a plastic, ophthalmologic or reconstructive surgical procedure.

The surgical needle includes a taper point profile designed to resist bending loads applied to the needle end, for example particularly during a grasping maneuver and/or manipulation of the needle. The taper point profile is defined by having cross-section diameters which dynamically increase over the length of the needle taper point end. More specifically, the taper point profile of the needle defines a varied taper angle which defines a significantly smaller taper ratio in a first region adjacent the tip of the needle thereby defining a generally parabolic shape to the needle than the taper ratio in a second region proximal of the first region, i.e., the diameter of the needle increases at a greater rate nearer the tip of the needle toward the main body portion thereof. Thus, the surgical needle defines an enlarged diameter taper point profile relative to conventional taper point needles. Consequently, the surgical needle is desirably more resistant to breakage upon grasping or manipulation of the needle during a given surgical procedure, while providing sufficient penetration performance for efficacious results in a particular procedure.

To illustrate this uniquely advantageous needle configuration an exemplary embodiment is shown in FIG. 1 the dimensions of which correspond to the data contained in Table 1 below. The distal tapered tip configuration of a surgical needle 10 is shown schematically to demonstrate the generally parabolic shape of the needle's tapered tip portion. The distal tapered tip portion extends from a base portion (not shown) of needle 10.

Table 1 below provides illustrative data which are representative of the diameter of the needle at various locations measured with reference from the needle point wherein X=0. The data are representative of an exemplary needle having a root diameter of 0.039 inches. As will be appreciated from reviewing the data, the diameter increases in a non-linear manner with the greatest rate of increase occurring in a first region defined by the region $X_3$-$X_0$ adjacent the needle tip and at a significantly reduced rate of increase for a second region of the tapered tip as defined by the region $X_{14}$-$X_3$. Each of the dimensions noted in the tables are approximate values and are expressed in inches. The first region represents approximately ⅕ of the overall length of the tapered portion of needle 10 and the second region represents approximately ⅘ of the overall length of the tapered portion of needle 10. The distance $Y_{14}$ is approximately half of the root diameter of the needle 10.

TABLE 1

| n | $X_n$ | $Y_n$ |
|---|---|---|
| 0 | 0.000 | 0.000 |
| 1 | 0.0120 | 0.0030 |
| 2 | 0.0319 | 0.0067 |
| 3 | 0.0519 | 0.0094 |
| 4 | 0.0719 | 0.0116 |
| 5 | 0.0919 | 0.0131 |
| 6 | 0.1120 | 0.0143 |
| 7 | 0.1320 | 0.0154 |
| 8 | 0.1520 | 0.0164 |
| 9 | 0.1722 | 0.0171 |
| 10 | 0.1920 | 0.0176 |
| 11 | 0.2120 | 0.0181 |
| 12 | 0.2320 | 0.0187 |
| 13 | 0.2522 | 0.0192 |
| 14 | 0.2724 | 0.0195 |

The taper ratio of the tapered portion of needle 10 is defined according to the following equation:

$$\text{Taper Ratio} = (X_{n2} - X_{n1})/(2Y_{n2})$$

where: $X_{n1}$=the point along the needle taper segment which is closest to the tip;

$X_{n2}$=the point along the needle taper segment which is further away from the tip; and $2Y_{n2}$=the diameter of the needle which intersects the point $X_{n2}$.

Since the rate of change of the diameter along the length of the tapered portion increases along the length of the tapered portion approaching the end at $X_0$, the application of the above equation will yield an average taper ratio for the length of the region determined by the X end points of the particular region being considered. Thus, with reference to FIG. 1 and Table 1, the average taper ratio of the first region defined by $X_3$-$X_0$ is approximately 2.76:1. The average taper ratio of the second region as defined by $X_{14}$-$X_3$ is approximately 5.65:1.

The surgical needle 10 may be curved or straight. The needle body may have a variety of cross-sections and may be flat pressed to facilitate gripping engagement with a grasping tool. The butt end (not shown) of the needle has a bore or channel for reception of a suture. The butt end may be crimped, swaged, etc. to facilitate attachment of the suture to the needle. The use of adhesives is also envisioned.

The choice of materials of surgical needle 10 is made to optimize strength, ductility and resistance to bending or breaking of the needle. However, as noted, the cross-sectional shape and dimensions of the needle contributes significantly to the physical characteristics of the needle. Preferred materials include stainless steel such as series "300" stainless steels, which typically have tensile strengths of between 325,000–350,000 lbs/in.sup.2, attain their high strength from undergoing cold working as the material is converted from an ingot to wire of the desired diameter.

Surgical needle 10 is manufactured through conventional cutting, coining, grinding and/or swaging processes, and may be heat treated to further enhance its strength and resistance to bending.

Although the illustrative embodiments of the present disclosure have been described herein with reference to the accompanying drawings, it is to be understood that the disclosure is not limited to those precise embodiments, and that various other changes and modifications may be affected therein, by one skilled in the art, without departing from the scope or spirit of the disclosure. All such changes and modifications are intended to be included within the scope of the disclosure as defined by the appended claims.

What is claimed is:

1. A surgical needle which comprises:
   a base portion having a root diameter; and
   a tapered end portion extending from said base portion to a pointed end, the tapered end portion defining at least a first and second region, the first region having an average taper ratio of approximately 2.76:1 and the second region having an average taper ratio of approximately 5.65:1.

2. The surgical needle according to claim 1 wherein the first region incorporates a length which is approximately ⅕ of the overall length of the tapered end portion.

3. A surgical needle, which comprises:
   an elongated needle member including a base portion having a root diameter and a needle end portion extending to a needle tip, the needle end portion defining a non-linear tapered configuration and being devoid of edges, the needle end portion defining a first region adjacent the needle tip and a second region adjacent the first region, the first region having an average taper ratio less than about 3:1, the second region having an average taper ratio less than about 6:1.

4. The surgical needle according to claim 3 wherein the first region incorporates a length which is at least about ⅕ of the overall length of the tapered end portion.

5. The surgical needle according to claim 3 wherein the needle end portion defines a general parabolic configuration.

6. A surgical needle, which comprises:
   an elongated needle member including a base portion having a root diameter and a needle end portion extending to a needle tip, the needle end portion being devoid of an edge and defining a first region adjacent the needle tip and a second region adjacent the first region, the first region having an average taper ratio of less that about 3:1 and the second region having an average taper ratio of less than about 6:1.

7. The surgical needle according to claim 6 wherein the needle end portion defines a non-linear tapered configuration.

8. The surgical needle according to claim 6 wherein the needle tip is pointed.

* * * * *